United States Patent
Kfoury et al.

(10) Patent No.: US 9,683,986 B2
(45) Date of Patent: Jun. 20, 2017

(54) TREATMENT OF CANCER BY INHIBITION OF THE MYD88/ERK MAP KINASE INTERACTION

(71) Applicants: CENTRE LEON BERARD, Lyons (FR); UNIVERSITE CLAUDE BERNARD LYON 1, Villeurbanne (FR); HOSPICES CIVILS DE LYON, Lyons (FR); INSTITUT NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR)

(72) Inventors: Alain Kfoury, Lyons (FR); Isabelle Coste-Invernizzi, Chazey d'Azergues (FR); Serge Lebecque, Civrieux d'Azergues (FR); Toufic Renno, Civrieux d'Azergues (FR)

(73) Assignees: CENTRE LEON BERARD, Lyons (FR); UNIVERSITE CLAUDE BERNARD LYON 1, Villeurbanne (FR); HOSPICES CIVILS DE LYON, Lyons (FR); INSTITUTE NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 131 days.

(21) Appl. No.: 14/364,582

(22) PCT Filed: Dec. 17, 2012

(86) PCT No.: PCT/EP2012/075839
§ 371 (c)(1),
(2) Date: Jun. 11, 2014

(87) PCT Pub. No.: WO2013/087937
PCT Pub. Date: Jun. 20, 2013

(65) Prior Publication Data
US 2014/0329261 A1 Nov. 6, 2014

(30) Foreign Application Priority Data
Dec. 16, 2011 (EP) .................... 11306686

(51) Int. Cl.
C12Q 1/48 (2006.01)
G01N 33/50 (2006.01)
G01N 33/573 (2006.01)

(52) U.S. Cl.
CPC ...... *G01N 33/5011* (2013.01); *G01N 33/5023* (2013.01); *G01N 33/5026* (2013.01); *G01N 33/573* (2013.01); *G01N 2333/91205* (2013.01); *G01N 2500/02* (2013.01); *G01N 2500/10* (2013.01)

(58) Field of Classification Search
CPC .......... G01N 33/5011; G01N 33/5023; G01N 33/5026; G01N 33/573; G01N 2333/91205; G01N 2500/02; G01N 2500/10
See application file for complete search history.

(56) References Cited

U.S. PATENT DOCUMENTS

2006/0141490 A1 6/2006 Coste-Invernizzi et al.
2010/0069297 A1 3/2010 Fenton et al.
2010/0151050 A1 6/2010 Mizuarai et al.

OTHER PUBLICATIONS

Silasi D-A. et al., "MyD88 predicts chemoresistance to paclitaxel in epithelial ovarian cancer", Yale Journal of Biology and Medicine, 2006, vol. 79, pp. 153-163.*
Bartz S.R. et al., "Small Interfering RNA Screens Reveal Enhanced Cisplatin Cytotoxicity in Tumor Cells Having both BRCA Network and TP53 Disruptions", Molecular and Cellular Biology, Dec. 2006, vol. 26, No. 24, pp. 9377-9386.*
Rakoff-Nahoum, Seth, et al; "Regulation of spontaneous intestinal tumorigenesis through the adaptor protein MyD88," Science, vol. 31, Jul. 6, 2007, pp. 124-127.
Dai, Yun, et al. : "Interruption of the Ras/MEK/ERK signaling cascade enhances Chk1 inhibitor-induced DNA damage in vitro and in vivo in human multiple myeloma cells," Sep. 15, 2008, Blood 112 (6).
Lee, Sung Hee, et al: "ERK activation drives intestinal tumorigenesis in Apcmin/+mice," Nature Medicine, vol. 16, No. 6, Jun. 1, 2010, pp. 665-670, XP055017197.
Coste, Isabelle, et al: "Dual function of MyD88 in RAS signaling and inflammation, leading to mouse and human cell transformation", Journal of Clinical Investigation, vol. 120, No. 10, Oct. 1, 2010, pp. 3663-3667, XP055017174.
Sun, Zujun, et al: "Role of toll-like receptor 4 on the immune escape of human oral squamous cell carcinoma and resistance of cisplatin-induced apoptosis", Molecular Cancer, Biomed Central, London, vol. 11, No. 1, May 14, 2012, p. 33, XP021121539.

* cited by examiner

*Primary Examiner* — Satyendra K Singh
(74) *Attorney, Agent, or Firm* — Harness, Dickey & Pierce, P.L.C.

(57) ABSTRACT

A method for selecting in vitro compounds is capable of potentiating the effect of a DNA damage inducing chemotherapy agent for the treatment of cancer, and includes selecting compounds inhibiting the interaction between MyD88 and ERK MAP KINASE.

10 Claims, 3 Drawing Sheets

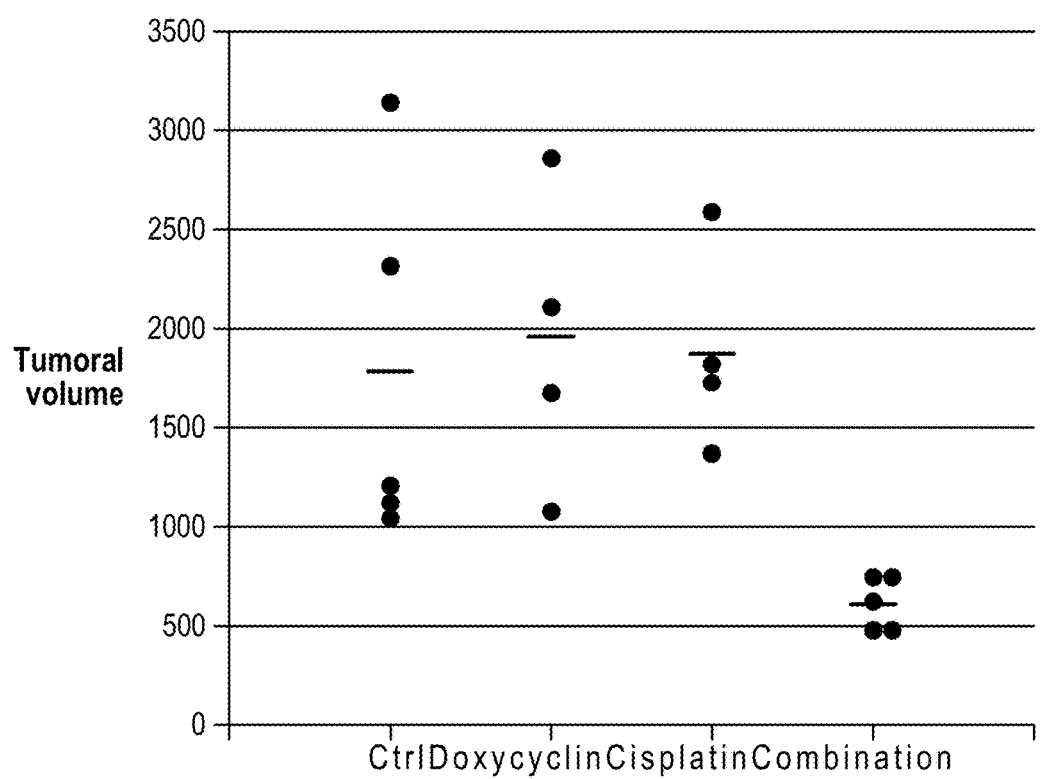

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence

```
<220> FEATURE:
<223> OTHER INFORMATION: siRNA MyD2

<400> SEQUENCE: 1
ggaaugugac uuccagaccu u                                              21

<210> SEQ ID NO 2
<211> LENGTH: 23
<212> TYPE: DNA
<213> ORGANISM: Artificial Sequence
<220> FEATURE:
<223> OTHER INFORMATION: siRNA MyD3

<400> SEQUENCE: 2
auuugcacuc agccucucuu uuu                                            23

<210> SEQ ID NO 3
<211> LENGTH: 22
<212> TYPE: DNA
<213> ORGANISM: Artificial Sequence
<220> FEATURE:
<223> OTHER INFORMATION: shRNAmir sense

<400> SEQUENCE: 3
cggaccctaa atccaataga aa                                             22

<210> SEQ ID NO 4
<211> LENGTH: 22
<212> TYPE: DNA
<213> ORGANISM: Artificial Sequence
<220> FEATURE:
<223> OTHER INFORMATION: shRNAmir antisense

<400> SEQUENCE: 4
tttctattgg atttagggtc ct                                             22

<210> SEQ ID NO 5
<211> LENGTH: 97
<212> TYPE: DNA
<213> ORGANISM: Artificial Sequence
<220> FEATURE:
<223> OTHER INFORMATION: Human TRIPZ lentiviral inducible shRNAmir

<400> SEQUENCE: 5
tgctgttgac agtgagcgcg gaccctaaat ccaatagaaa tagtgaagcc acagatgtat    60
ttctattgga tttagggtcc ttgcctactg cctcgga                             97
```

TREATMENT OF CANCER BY INHIBITION OF THE MYD88/ERK MAP KINASE INTERACTION

CROSS-REFERENCE TO RELATED APPLICATIONS

This application is a National Phase Entry of International Application No. PCT/EP2012/075839, filed on Dec. 17, 2012, which claims priority to European Patent Application Serial No. 11306686.4, filed on Dec. 16, 2011, both of which are incorporated by reference herein.

BACKGROUND AND SUMMARY

The present invention relates to methods for identifying novel compounds for use in the treatment of cancer and to compounds inhibiting the MyD88/Erk MAP kinase interaction for treating cancer.

It is well established that inflammation acts as a promoter of carcinogenesis. MyD88, an adaptor protein in the TLR signaling pathway, has therefore been implicated in carcinogenesis through its role in inflammation.

The present invention now surprisingly shows that MyD88 plays an intrinsic role in ras-dependent carcinogenesis in vitro and in vivo. Specifically, MyD88 binds ERK MAP Kinase through a conserved motif, blocking therefore the inactivation of ERK by its specific phosphatase MKP3, and leading to the amplification of the activity of the ras canonical pathway. The relevance of this mechanism in human cancers is demonstrated, MyD88 appears overexpressed and associated to phospho-ERK in many human cancers. Moreover, the experimental data shows that MyD88 participates directly in the ras signaling pathway and in the malignant transformation induced by this oncogene.

Inhibitors of the MyD88/Erk MAP Kinase interaction induce apoptosis in tumor cells. Interestingly, a synergistic effect is observed between inhibitors of the MyD88/Erk MAP kinase and DNA damage inducing chemotherapy. The present invention therefore provides new therapeutic perspectives in cancers, where the first line therapy is based on DNA damage inducing chemotherapy agents. Combination of DNA damage inducing chemotherapy agents with inhibition of the MyD88/Erk MAP kinase interaction enables dose reduction in sensitive tumors and therefore increases patient tolerance or re-induces sensitivity in resistant cancer cell lines having highly efficient DNA repair mechanisms.

1) The present invention is related to methods for selecting in vitro compounds capable of potentiating the effect of a DNA damage inducing chemotherapy agent for the treatment of cancer comprising the following steps:
  a) Providing at least one candidate compound;
  b) Contacting at least one candidate compound with a ERK MAPK protein and a MyD88 protein, under conditions suitable to allow ERK MAPK and MyD88 to interact in the absence of the candidate molecule;
  c) Determining the interaction of ERK MAPK and MyD88 as measured in the presence and in the absence of at least one candidate compound; and
  d) Selecting a candidate compound inhibiting the interaction of ERK MAPK and MyD88.

2) Method for selecting in vitro compounds capable of potentiating the effect of a DNA damage inducing chemotherapy agent for the treatment of cancer according to 1, wherein one or both of ERK MAPK and MyD88 are attached to a detectable label.

3) Method for selecting in vitro compounds capable of potentiating the effect of a DNA damage inducing chemotherapy agent for the treatment of cancer according to anyone of 1-2, wherein the interaction of ERK MAPK and MyD88 is determined using a two-hybrid system, affinity chromatography, co-immunoprecipitation, subcellular fractionation and isolation of large molecular complexes, immunoblotting, immunolabelling, a proximity ligation assay, an immunoprecipitation assay, a biacore assay or a GST pull-down assay.

4) Method for selecting in vitro compounds capable of potentiating the effect of a DNA damage inducing chemotherapy agent for the treatment of cancer according to anyone of 1-3, wherein the DNA damage inducing chemotherapy agent is selected in the group consisting of oxaliplatin, cisplatin, carboplatin, doxorubicin, etoposide, bleomycin, and mixtures thereof.

5) Method for selecting in vitro compounds capable of potentiating the effect of a DNA damage inducing chemotherapy agent for the treatment of cancer according to anyone of 1-4, wherein the cancer is selected in the group consisting of colorectal cancer, intestinal cancer, melanoma, lung cancer and cervical cancer.

6) Method for selecting in vitro compounds capable of potentiating the effect of a DNA damage inducing chemotherapy agent for the treatment of cancer comprising the following steps:
  a) Providing at least one candidate compound;
  b) Providing transformed cells expressing stably MyD88 under the control of an inducible promoter and expressing a reporter gene under the control of a promoter from the MAPK pathway selected from the SRE promoter, the ELK promoter and the MyC promoter;
  c) Inducing overexpression of MYD88 in said transformed cells in the presence of at least one candidate compound;
  d) Measuring the expression of the reporter gene and selecting at least a candidate compound inhibiting the expression of the reporter gene;
  e) Providing immortalized fibroblasts transformed by transfection with the MyD88 and Myc oncogenes;
  f) Monitoring focus formation in the presence of at least one candidate compound selected in step d) and in the presence of at least one DNA damage inducing chemotherapy agent, and selecting a candidate compound potentiating the inhibitory effect of the DNA damage inducing chemotherapy agent on focus formation.

7) Method for selecting in vitro compounds capable of potentiating the effect of a DNA damage inducing chemotherapy agent for the treatment of cancer according to 6, wherein in step b) the promoter from the MAPK pathway is the SRE promoter.

8) Method for selecting in vitro compounds capable of potentiating the effect of a DNA damage inducing chemotherapy agent for the treatment of cancer according to anyone of 6-7, wherein the method further comprises the following steps:
  Providing transformed cells expressing stably MyD88 under the control of an inducible promoter and expressing a reporter gene under the control of a promoter from the inflammation pathway selected from the Nf-kB promoter and the ISRE promoter;
  Inducing overexpression of MYD88 in said transformed cells in the presence of at least one candidate compound;

Measuring the expression of the reporter gene and selecting a candidate compound which does not inhibit the expression of the reporter gene.

9) Method for selecting in vitro compounds capable of potentiating the effect of a DNA damage inducing chemotherapy agent for the treatment of cancer according to 8, wherein the promoter from the inflammation pathway is Nf-kB.

10) Method for selecting in vitro compounds capable of potentiating the effect of a DNA damage inducing chemotherapy agent for the treatment of cancer according to anyone of 6-9, wherein in step b) the cells are selected from the HCT116 cell line, the A375 cell line and a HeLa cell line.

11) Method for selecting in vitro compounds capable of potentiating the effect of a DNA damage inducing chemotherapy agent for the treatment of cancer according to anyone of 6-10, wherein the inducible promoter is an antibiotic-inducible promoter.

12) Method for selecting in vitro compounds capable of potentiating the effect of a DNA damage inducing chemotherapy agent for the treatment of cancer according to anyone of 6-11, wherein the reporter gene is luciferase.

13) Method for selecting in vitro compounds capable of potentiating the effect of a DNA damage inducing chemotherapy agent for the treatment of cancer according to anyone of 6-12, wherein the immortalized fibroblasts are NIH3T3 immortalized fibroblasts.

14) Method for selecting in vitro compounds capable of potentiating the effect of a DNA damage inducing chemotherapy agent for the treatment of cancer according to anyone of 6-13, wherein the cancer is selected in the group consisting of colorectal cancer, intestinal cancer, melanoma, lung cancer and cervical cancer.

15) Method for selecting in vitro compounds capable of potentiating the effect of a DNA damage inducing chemotherapy agent for the treatment of cancer according to anyone of 6-14, wherein the DNA damage inducing chemotherapy agent is selected from oxaliplatin, cisplatin, carboplatin, doxorubicin, etoposide and mixtures thereof.

16) Method for selecting in vitro compounds capable of potentiating the effect of a DNA damage inducing chemotherapy agent for the treatment of cancer according to anyone of 6-14, wherein the at least one candidate compound of step a) is selected according to a method according to anyone of 1-5.

The present invention is related to an in vitro method for selecting a compound for the treatment of cancer comprising the following steps:
a) Providing candidate compounds;
b) Providing transformed cells expressing stably MyD88 under the control of an inducible promoter and expressing a reporter gene under the control of a promoter from the MAPK pathway selected from the SRE promoter, the ELK promoter and the MyC promoter;
c) Inducing overexpression of MYD88 in said transformed cells in the presence of the candidate compound;
d) Measuring the expression of the reporter gene and selecting a candidate compound inhibiting the expression of the reporter gene;
e) Providing immortalized fibroblasts transformed by transfection with the MyD88 and Myc oncogenes;
f) Monitoring focus formation in the presence of the candidate compound selected in step d) and selecting said compound if focus formation is inhibited. Preferably, in the methods of the present invention the promoter from the MAPK pathway in step b) is the SRE promoter.

In preferred embodiments, the methods of the present invention further comprise the following steps:
Providing transformed cells expressing stably MyD88 under the control of an inducible promoter and expressing a reporter gene under the control of a promoter from the inflammation pathway selected from the Nf-kB promoter and the ISRE promoter;
Inducing overexpression of MYD88 in said transformed cells in the presence of the candidate compound;
Measuring the expression of the reporter gene and selecting a candidate compound which does not inhibit the expression of the reporter gene.

Preferably, the promoter from the inflammation pathway is the Nf-kB promoter.

In preferred embodiments, the cells are selected from the HCT116 cell line, the A375 cell line and a HeLa cell line in the methods of the present invention. Preferably, the inducible promoter is an antibiotic-inducible promoter. Preferably, the reporter gene is luciferase. In the methods of the present invention, the immortalized fibroblasts are preferably NIH3T3 immortalized fibroblasts.

The present invention is also related to an in vitro method for selecting a compound for the treatment of cancer comprising determining whether said compound inhibits the interaction between the MyD88 protein and the ERK MAP kinase by a proximity ligation assay, an immunoprecipitation assay, a biacore assay, a GST pull-down assay or a yeast two hybrid system. The present invention is also related to a compound inhibiting the interaction of MyD88 and ERK MAP kinase selected from peptides inhibiting the interaction of MyD88 with ERK MAP kinase and interfering RNA inhibiting the expression of human Myd88, for use in the treatment of cancer by inducing apoptosis in cancer cells. Preferably, the compounds according to the present invention are for use in treatment of cancers selected from colorectal cancer, intestinal cancer, melanoma, lung cancer and cervical cancer. Advantageously, the cancer is colorectal cancer.

The present invention also relates to a composition comprising a DNA damage inducing chemotherapy agent and a compound inhibiting the interaction of MyD88 with ERK MAP kinase selected from peptides inhibiting the interaction of MyD88 with ERK MAP kinase and interfering RNA inhibiting the expression of human Myd88, for use in the treatment of cancer. The present invention further relates to a composition comprising a compound inhibiting the interaction of MyD88 with ERK MAP kinase selected from peptides inhibiting the interaction of MyD88 with ERK MAP kinase and interfering RNA inhibiting the expression of human Myd88, for use in combination with DNA damage inducing chemotherapy agents in the treatment of cancer. In the methods and compositions of the present invention, the DNA damage inducing chemotherapy agent is preferably selected from oxaliplatin, cisplatin, carboplatin, doxorubicin, etoposide and mixtures thereof. The present invention is also directed to kits of part comprising a DNA damage inducing chemotherapy agent and a compound inhibiting the interaction of MyD88 with ERK MAP kinase selected from peptides inhibiting the interaction of MyD88 with ERK MAP kinase and interfering RNA inhibiting the expression of human Myd88, for use in the treatment of cancer.

SEQUENCE LISTING

SEQ ID No. 1: anti-MyD88 siRNA MyD2
SEQ ID No. 2: anti-MyF88 si RNA MyD3
SEQ ID No. 3: anti-MyD88 shRNAmir sense
SEQ ID No. 4: anti-MyD88 shRNAmir antisense
SEQ ID No. 5: anti-MyD88 shRNAmir

DETAILED DESCRIPTION

It is well established that inflammation acts as a promoter of carcinogenesis. MyD88, an adaptor protein in the TLR signaling pathway, has therefore been implicated in carcinogenesis through its role in inflammation. The present invention now surprisingly shows that MyD88 plays an intrinsic role in ras-dependent carcinogenesis in vitro and in vivo. Inhibition of MyD88 reduces carcinogenesis in vitro and in vivo by inducing apoptosis in cancer cells. A synergistic effect is observed with DNA damage inducing chemotherapy.

The present invention relates to methods for selecting and identifying compounds specifically inhibiting MyD88 activity through the MAPK/ERK pathway. These compounds inhibit DNA repair and therefore potentiate the effect of DNA damage inducing chemotherapy agent classically used in the treatment of cancer.

The term "MyD88" refers to the Myeloid differentiation primary response polypeptide or gene identified by Gene Bank number U70451.1 (21-03-1997). MyD88 has been described as an adaptor protein in the TLR signaling pathway. In the inflammation pathway MyD88 activates the transcription factor NF-κB. The present invention now surprisingly shows that MyD88 is involved in activation of the MAPK/ERK pathway.

The terms "ERK MAP kinase" refer to the Extracellular regulated kinase gene identified by Gene Bank number (Gene ID: 5595, NG_029936.1). The protein encoded by this gene is a member of the MAP kinase family. MAP kinases, also known as extracellular signal-regulated kinases (ERKs), act in a signaling cascade that regulates various cellular processes such as proliferation, differentiation, and cell cycle progression in response to a variety of extracellular signals. This kinase is activated by upstream kinases, resulting in its translocation to the nucleus where it phosphorylates nuclear targets.

The terms "compound potentiating the effect of a DNA damage inducing chemotherapy agent" refers to compounds capable to enhance or increase the effect of a DNA damage inducing chemotherapy agent. These compounds may have a synergistic effect with the DNA damage inducing chemotherapy agent. "Synergy" is defined as the joint effect of two drugs taken together being greater than the sum of the effects of the two drugs alone. These compounds may also render tumor cells which are resistant to DNA damage inducing chemotherapy agents, sensitive to these DNA damage inducing chemotherapy agents. These compounds are capable of making more active or more effective DNA damage inducing chemotherapy agents. Combination of DNA damage inducing chemotherapy agents with inhibition of the MyD88/Erk MAP kinase interaction enables dose reduction in sensitive tumors and therefore increases patient tolerance or re-induces sensitivity in resistant cancer cell lines having highly efficient DNA repair mechanisms.

The terms "DNA damage inducing chemotherapy agent" refer to chemical agents that cause DNA adducts, irreversible modification of DNA nucleotides, or breakage of DNA strands. Although repair systems can fix minor damage, cell death results if the damage cannot be repaired. These agents comprise different families of compounds used in the treatment of cancer, in particular cancers with a mutation or activation of one or more components of the Ras pathway (e.g. EGFR, Ras, Raf, B-Raf, MEK, Erk, and others) such as cancers of the colon, intestine, lung, breast, hematopoietic, stomach, prostate, etc. The DNA damage inducing chemotherapy agent is preferably selected from oxaliplatin, cisplatin, carboplatin, doxorubicin, etoposide, bleomycin and mixtures thereof.

The present invention is related to methods for selecting in vitro compounds capable of potentiating the effect of a DNA damage inducing chemotherapy agent for the treatment of cancer comprising the following steps:
 a) Providing at least one candidate compound;
 b) Contacting at least one candidate compound with a ERK MAPK protein and a MyD88 protein, under conditions suitable to allow ERK MAPK and MyD88 to interact in the absence of the candidate molecule;
 c) Determining the interaction of ERK MAPK and MyD88 as measured in the presence and in the absence of at least one candidate compound; and
 d) Selecting a candidate compound inhibiting the interaction of ERK MAPK and MyD88.

In the methods of the present invention, one or both of ERK MAPK and MyD88 are preferably attached to a detectable label. In the methods of the present invention, the interaction of ERK MAPK and MyD88 is preferably determined using a two-hybrid system, affinity chromatography, co-immunoprecipitation, subcellular fractionation and isolation of large molecular complexes, immunoblotting, immunolabelling, a proximity ligation assay, an immunoprecipitation assay, a biacore assay or a GST pull-down assay. In the methods of the present invention, the DNA damage inducing chemotherapy agent is selected in the group consisting of oxaliplatin, cisplatin, carboplatin, doxorubicin, etoposide, bleomycin, and mixtures thereof. The methods of the present invention are preferably for selecting compounds for use in the treatment of a cancer selected in the group consisting of colorectal cancer, intestinal cancer, melanoma, lung cancer and cervical cancer.

The invention more particularly relates to a method of screening or selecting candidate compounds wherein a candidate compound is assayed for its capacity to modulate the MyD88 protein and the ERK MAP kinase interaction, i.e. of preventing the binding of MyD88 with ERK MAP kinase, or also to dissociate, partly or totally, the so-formed MyD88/ERK MA Kinase complexes. Preferably, the invention relates to method of screening compounds capable of modulating the MyD88/ERK MAPK interaction, and in particular of compounds useful for the treatment of cancer, wherein an antagonist of the MyD88/ERK MAPK interaction is identified. The candidate compound may be assayed for its capacity to interfere with or disrupt the interaction of MyD88 with ERK MAPK. Advantageously, a MyD88 protein, a ERK MAPK protein and at least one candidate compound are contacted and incubated under conditions suitable to allow them to interact, and in particular to dissociate ERK MAPK/MyD88 complexes. Alternatively, a MyD88 protein and a ERK MAPK protein are contacted under conditions suitable to formation of ERK MAPK/MyD88 complexes. At least one candidate compound is further added and the three components are contacted under conditions suitable to allow them to interact, and optionally to allow ERK MAPK/MyD88 complexes to dissociate.

Determining of the capacity of the candidate compound to modulate the interaction of MyD88 with ERK MAPK, or to bind and modulate a MyD88/ERK MAPK complex, can be achieved by any appropriate mean well-known by the one skilled in the art, such as classical separation and/or detection methods. For instance, MyD88/ERK MAPK complexes may be quantified in the presence of increasing concentrations of candidate compounds MyD88/ERK MAPK binding can be carried out using classical analysis procedures such as in vitro assays of protein or peptide binding, e.g., wherein one or both of the MYD88 or ERK MAPK components are attached to a detectable label (BRET, FRET, HTRF), and/or are immobilized may be employed. In general, methods classically used for the detection of a positive protein-protein interaction, such as two-hybrid system, affinity chromatography, co-immunoprecipitation, subcellular fractionation and isolation of large molecular complexes, immunoblotting, or immunolabelling, proximity ligation assay, an immunoprecipitation assay, a biacore assay, a GST pull-down assay or a yeast two hybrid system optionally in association with detectable markers such as fluorescent, isotopic or chromogenic labelling, can also be used to identify compounds that interfere or disrupt said interaction.

The present invention also relates to methods for selecting in vitro compounds capable of potentiating the effect of a DNA damage inducing chemotherapy agent for the treatment of cancer comprising the following steps:
  a) Providing at least one candidate compound;
  b) Providing transformed cells expressing stably MyD88 under the control of an inducible promoter and expressing a reporter gene under the control of a promoter from the MAPK pathway selected from the SRE promoter, the ELK promoter and the MyC promoter;
  c) Inducing overexpression of MYD88 in said transformed cells in the presence of at least one candidate compound;
  d) Measuring the expression of the reporter gene and selecting at least a candidate compound inhibiting the expression of the reporter gene;
  e) Providing immortalized fibroblasts transformed by transfection with the MyD88 and Myc oncogenes;
  f) Monitoring focus formation in the presence of at least one candidate compound selected in step d) and in the presence of at least one DNA damage inducing chemotherapy agent, and selecting a candidate compound potentiating the inhibitory effect of the DNA damage inducing chemotherapy agent on focus formation.

The methods of the present invention provide for selection of compounds inhibiting activation of the MAPK/ERK pathway by MyD88. The terms "MAPK pathway", "ERK pathway" and "MAPK/ERK pathway" are use indifferently herein and refer to a signal transduction pathway involving a cascade of protein kinase regulating transcription of various genes. This pathway has been implicated in various cancers.

Any candidate compound may be selected in the methods of the present invention. In preferred embodiments, the candidate compound is a small compound capable of diffusing into a cell such as a chemical compound or a peptide.

The assays of the present invention are based on transformed cells expressing both MyD88 under the control of an inducible promoter and expressing a reporter gene under the control of a promoter from the MAPK pathway selected from the SRE promoter, the ELK promoter and the MyC promoter. Any suitable cells may be used in the methods of the present invention; preferably the cells are eukaryotic cells and most preferably mammalian cells. Immortalized cell lines are preferred in the methods of the present invention. Advantageously, the cells are selected from the group consisting of the HCT116 cell line, the A375 cell line and HeLa cell lines. Cells are transformed according to known techniques.

MyD88 is expressed in the transformed cells under the control of an inducible promoter. Any inducible promoters and any factor activating them known to the skilled person may be used in the methods of the present invention. In preferred embodiments, the inducible promoter is an antibiotic-inducible promoter and the factor/inducer is an antibiotic. In a preferred embodiment, the promoter is inducible by doxycyclin.

The transformed cells further express a reporter gene under the control of a promoter from the MAPK pathway selected from the SRE promoter, the ELK promoter and the MyC promoter. Any reporter gene whose expression is easily identified and measured may be used in the methods of the present invention. Luciferase and GFP are examples of commonly used reporter genes. In preferred embodiments, the reporter gene is luciferase. The reporter gene whose activity is measured is expressed under the control of the SRE promoter, the ELK promoter or the MyC promoter.

The terms "SRE promoter" refer to "Serum response elements", which is a DNA sequence (CC(A/T)6GG) that is used upstream of reporter genes and is known to be the binding site of the SRF (Serum response factor) proteins encoded by SRF gene identified by Gene Bank number (Gene ID: 6722, NM_003131.2).

The terms "ELK promoter" refer to the promoter of the E twenty-six (ETS)-like transcription factor gene identified by Gene Bank number (Gene ID: 2002, NG_009222.1). The protein encoded by this gene is a nuclear target for the ras-raf-MAPK signaling cascade.

The terms "MyC promoter" refer to the promoter of the C-myelocytomatosis viral oncogene homolog gene identified by Gene Bank number (Gene ID: 4609, NG_007161.1). Myc is activated upon various mitogenic signals such as EGF (via the MAPK/ERK pathway). By modifying the expression of its target genes, Myc activation results in numerous biological effects, like driving cell proliferation, regulating cell growth, apoptosis, differentiation and stem cell self-renewal.

Preferably, in the methods of the present invention the promoter from the MAPK pathway in step b) is the SRE promoter. Overexpression of MyD88 is induced when the factor/inducer is added to the culture medium or turned off upon retrieval of the inducer. Overexpression of MyD88 activates the MAPK/ERK pathway. In the methods of the present invention overexpression of MyD88 is induced in the presence of the candidate compound. Inhibition of the ERK/MAPK pathway activation by MyD88 by the candidate compound is monitored by measuring the expression of the reporter gene under the control of a promoter from the MAPK/ERK pathway selected from SRE, ELK and MyC. Candidate compounds inhibiting the expression of the reporter gene in the transformed cells are selected in the methods of the present invention.

As MyD88 is known for activating the inflammation pathway, the methods of the present invention may advantageously comprise steps to eliminate compounds inhibiting the inflammation pathway or to select compounds, which do not significantly inhibit the inflammation pathway. The methods of the present invention may therefore also comprise the following steps:
  Providing transformed cells expressing stably MyD88 under the control of an inducible promoter and expressing a reporter gene under the control of a promoter from the inflammation pathway selected from the Nf-kB promoter and the ISRE promoter;
  Inducing overexpression of MYD88 in said transformed cells in the presence of the candidate compound;
  Measuring the expression of the reporter gene and selecting a candidate compound which does not inhibit the expression of the reporter gene. These additional steps are performed as described above.

The terms "Nf-kB promoter" refer to the promoter of the nuclear factor kappa-light-chain-enhancer of activated B cells, it is composed by a dimer of proteins p65 RELA/p50 encoded by genes identified by Gene Bank numbers (p65 RELA=Gene ID: 5970, NG_029971.1/p50=Gene ID: 4790, NM 001165412.1). NF-κB is clearly one of the most important regulators of proinflammatory gene expression. Synthesis of cytokines, such as TNF-α, IL-1β, IL-6, and IL-8, is mediated by NF-κB, as is the expression of cyclooxygenase 2 (Cox-2).

The terms "ISRE promoter" refer to Interferon-sensitive response element, a DNA sequence (TTTCAT) that is used upstream of reporter genes and is known to be the binding site of the STAT (Signal Transducers and Activators of Transcription protein) family proteins like STAT3 (NG_007370.1, NM_003150.3) and the IRF (Interferon response factors) family proteins like IRF3 (NG_031810.1, NM_001197122.1). The STAT pathway is one major signaling pathway converting the cytokine signal into gene expression programs regulating the proliferation and differentiation of the immune cells. Several members of the STAT protein family act as transcription factors in modulating pro- and anti-inflammatory responses.

Preferably, the promoter from the inflammation pathway is the Nf-kB promoter. These additional steps select a compound, which does not interfere with the role of MyD88 in the inflammation pathway. They may be performed simultaneously or after selecting candidate compounds inhibiting activation of the MAPK/ERK pathway. The methods described above provide a candidate compound inhibiting activation of the MAPK/ERK pathway by MyD88 and advantageously not interfering with MyD88's role in the inflammation pathway.

The selected candidate compounds are further screened for their capability potentiate the inhibitory effect of DNA damage inducing chemotherapy agents on MyD88 activated carcinogenesis in fibroblasts. Immortalized fibroblasts are transformed with the MyD88 and Myc oncogenes. The term "Myc" refers to the C-myelocytomatosis viral oncogene homolog gene identified by Gene Bank number (Gene ID: 4609, NG_007161.1) Myc is activated upon various mitogenic signals such as EGF (via the MAPK/ERK pathway). By modifying the expression of its target genes, Myc activation results in numerous biological effects, like driving cell proliferation, regulating cell growth, apoptosis, differentiation and stem cell self-renewal.

In the methods of the present invention, the immortalized fibroblasts are preferably NIH3T3 immortalized fibroblasts. Focus formation of the fibroblasts is monitored in the presence of at least one candidate compound selected as described above and in the presence of at least one DNA damage inducing chemotherapy agent. At least a candidate compound potentiating the inhibitory effect of DNA damage inducing chemotherapy agent on focus formation in in vitro cell culture is selected.

Preferably, the methods of the present invention provide for screening, identifying or selecting compounds for use in the treatment of cancer, wherein the cancer is selected in the group consisting of colorectal cancer, intestinal cancer, melanoma, lung cancer and cervical cancer. In the methods described above, the DNA damage inducing chemotherapy agent is preferably selected from oxaliplatin, cisplatin, carboplatin, doxorubicin, etoposide, bleomycin and mixtures thereof. Another object of the present invention is a compound inhibiting the interaction of MyD88 and ERK MAP kinase selected from peptides inhibiting the interaction of MyD88 with ERK MAP kinase and interfering RNA inhibiting the expression of human MyD88, for use in the treatment of cancer by inducing apoptosis in cancer cells. The term "peptide" refers to peptides and modified peptides.

In preferred embodiments the compound inhibiting the interaction of MyD88 and ERK MAP kinase is an interfering RNA inhibiting the expression of human MyD88. The interfering RNA molecules are used to specifically target messenger RNA (Mrna): the interfering RNA hybridizes with the Mrna and consequently inhibits the translation of the corresponding protein, either by simple steric hindrance or by promoting Mrna cleavage. The interfering RNA can be chosen from a plurality of forms, such as: antisense RNA, double-stranded RNA, "small interfering" RNA (siRNA), "Small Hairpin" RNA (shRNA) or ribosomal RNA.

The siRNA, for "Small Interfering RNA" are short sequences of around 15 to 30 base pairs. They include a first strand and an additional strand identical to the targeted region of the RNA of the target gene. The shRNA for "Small Hairpin RNA" are double-stranded RNA produced by a cloned sequence in an expression vector, coding for a RNA molecule that will adopt a hairpin shape after cleavage by the Dicer and loquacious complex. The design and preparation of interfering RNA and their use are well known and widely described in numerous publications.

In preferred embodiments, the siRNA is selected from the siRNA of SEQ ID No. 1 and the siRNA of SEQ ID No. 2. In another embodiment, the interfering RNA is a shRNAmir comprising the sequences of SEQ ID Nos. 3-4. Most preferably, the interfering RNA is the shRNAmir of SEQ ID No. 5.

The present invention also provides pharmaceutical compositions comprising:

a) an effective amount of a compound as described above, and b) a pharmaceutically acceptable carrier, which may be inert or physiologically active.

As used herein, "pharmaceutically-acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as combination thereof. In many cases, it will be preferable to include isotonic agents, such as sugars, polyalcohols, or sodium chloride in the composition. In particular, relevant examples of suitable carrier include: (1) Dulbecco's phosphate buffered saline, Ph ~7.4, containing or not containing about 1 mg/ml to 25 mg/ml human serum albumin, (2) 0.9% saline (0.9% w/v sodium chloride (NaCl)), and (3) 5% (w/v) dextrose; and may also contain an antioxidant such as tryptamine and a stabilizing agent such as Tween 20.

The pharmaceutical compositions encompassed by the present invention may also contain a further therapeutic agent for the treatment of cancers particularly for the treatment of colorectal cancer, intestinal cancer, melanoma, lung cancer and cervical cancer. The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperinoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects.

Sterile compositions for parenteral administration can be prepared by incorporating the compound in the required amount in the appropriate solvent, followed by sterilization by microfiltration. As solvent or vehicle, there may be used water, saline, phosphate buffered saline, dextrose, glycerol, ethanol, and the like, as well as combination thereof. In many cases, it will be preferable to include isotonic agents, such as sugars, polyalcohols, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions, which may be dissolved at the time of use in sterile water or any other injectable sterile medium.

The compositions comprising a compound as described herein may also be orally administered. As solid compositions for oral administration, tablets, pills, powders (gelatine capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavouring or stabilizing products. The doses depend on the desired effect, the duration of the treatment and the route of administration used.

The invention is also related to the use of a compound as described above for the manufacture of a medicament for treatment cancers and particularly for treatment of colorectal cancer, intestinal cancer, melanoma, lung cancer and cervical cancer. The present invention also provides methods for treating cancers including administering an effective amount of a compound as described above to a human or to a patient in need thereof. In a preferred embodiment, the invention relates to methods for treatment of colorectal cancer, intestinal cancer, melanoma, lung cancer and cervical cancer.

The present invention also relates to a composition comprising a DNA damage inducing chemotherapy agent and a compound inhibiting the interaction of MyD88 with ERK MAP kinase selected from peptides inhibiting the interaction of MyD88 with ERK MAP kinase and interfering RNA inhibiting the expression of human Myd88, for use in the treatment of cancer. The present invention also relates to methods for treating cancers including administering an effective amount of a DNA damage inducing chemotherapy agent and a compound inhibiting the interaction of MyD88 with ERK MAP kinase selected from peptides inhibiting the interaction of MyD88 with ERK MAP kinase and interfering RNA inhibiting the expression of human Myd88 to a human or to a patient in need thereof.

The DNA damage inducing chemotherapy agent and the compound inhibiting the interaction of MyD88 with ERK-MAP kinase may be administered simultaneously or separately. Combination of DNA damage inducing chemotherapy agents with inhibition of the MyD88/Erk MAP kinase interaction enables dose reduction in sensitive tumors and therefore increases patient tolerance or re-induces sensitivity in resistant cancer cell lines having highly efficient DNA repair mechanisms.

The present invention further relates to a composition comprising a compound inhibiting the interaction of MyD88 with ERK MAP kinase selected from peptides inhibiting the interaction of MyD88 with ERK MAP kinase and interfering RNA inhibiting the expression of human Myd88, for use in combination with DNA damage inducing chemotherapy agents in the treatment of cancer. In the methods and compositions of the present invention, the DNA damage inducing chemotherapy agent is preferably selected from oxaliplatin, cisplatin, carboplatin, doxorubicin, etoposide, bleomycin and mixtures thereof.

The present invention is also directed to kits of part comprising a DNA damage inducing chemotherapy agent and a compound inhibiting the interaction of MyD88 with ERK MAP kinase selected from peptides inhibiting the interaction of MyD88 with ERK MAP kinase and interfering RNA inhibiting the expression of human Myd88, for use in the treatment of cancer.

In preferred embodiments, the compounds and compositions of the present invention are for use in treatment of cancer and more particularly in treatment of colorectal cancer, intestinal cancer, melanoma, lung cancer and cervical cancer. Most advantageously, the compounds of the present invention are for use in the treatment of colorectal cancer. Advantageously, the compounds and compositions of the present invention are for use in the treatment of cancer by inducing apoptosis in cancer cells.

BRIEF DESCRIPTION OF THE FIGURES

FIG. 2: In vivo combination assay.

EXAMPLES

Figure 1A:
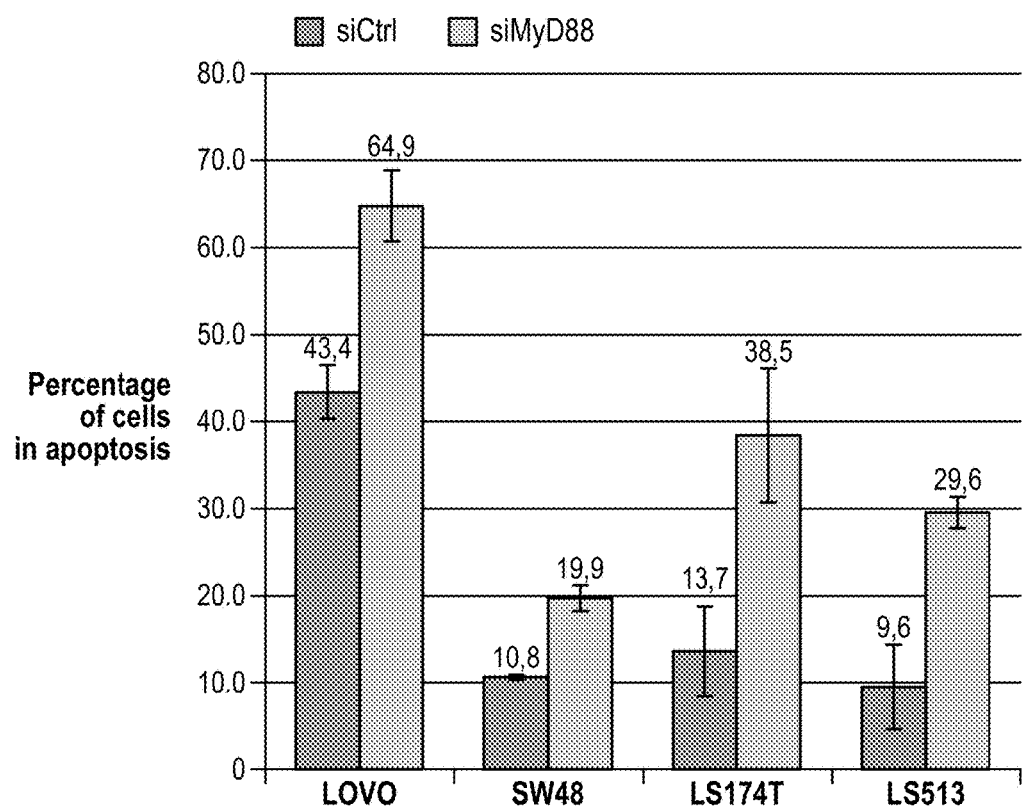
FIG. 1: MyD88 silencing induces a p53 dependent apoptosis in colon cancer cell lines. A-Apoptosis Analysis in different colon cancer cell lines upon Myd88 silencing by siRNA. B-Apoptosis analysis in HCT116 p53+/+ or p53−/− cells upon MyD88 silencing by two different siRNAs.
Figure 1A:
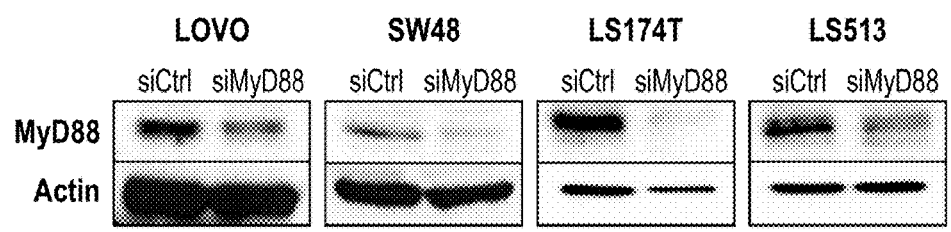
Figure 1B:
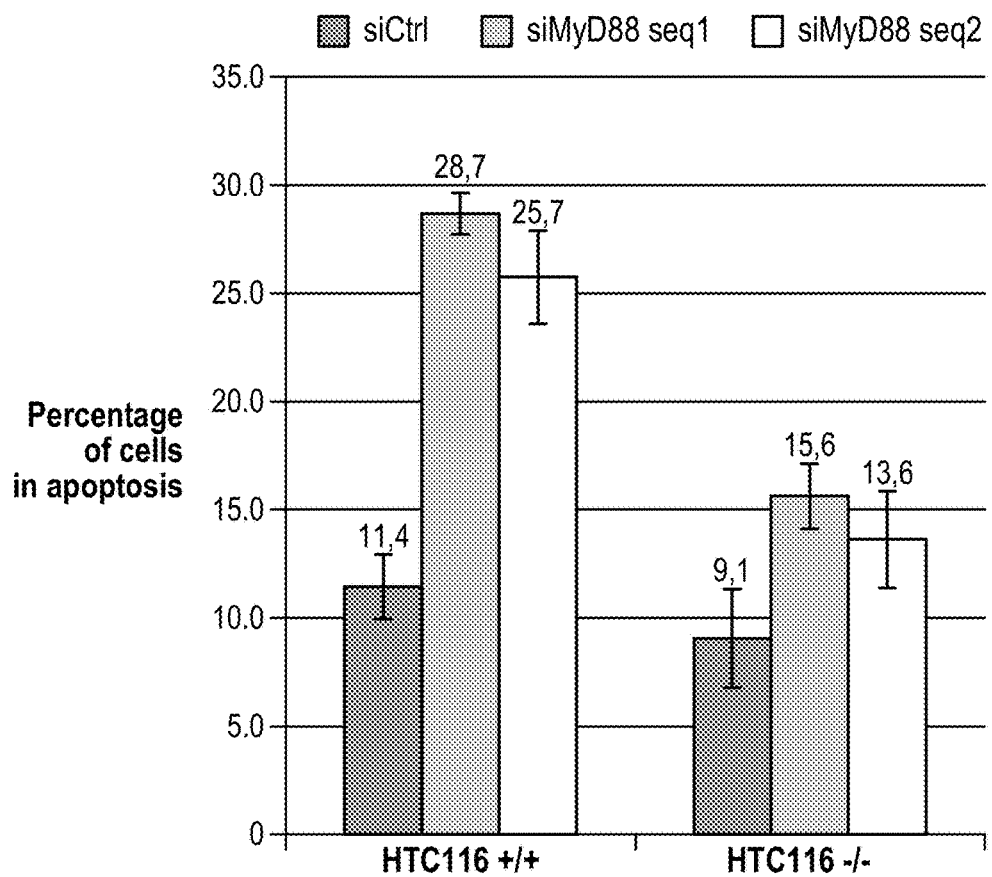
Figure 1B:
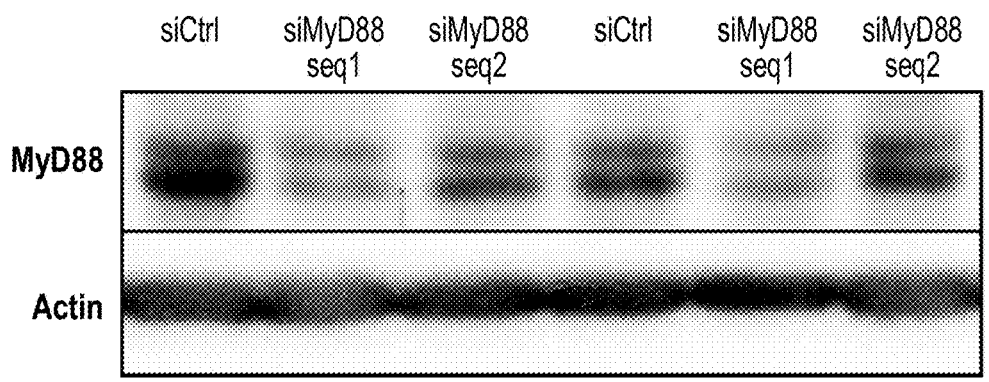

Example 1: MyD88 Extinction Activates p53 and Induces Apoptosis

Having previously shown that MyD88 is implicated in tumor initiation, we asked if MyD88 can play a role in the maintenance of the tumoral phenotype of established tumors. Upon MyD88 extinction by specific siRNA, cells undergo apoptosis. To elucidate the role of the tumor suppresser protein p53 in this apoptosis, we used the HCT116 p53+/+ or p53−/− cell lines. We observed a massive apoptosis upon MyD88 inhibition in the p53+/+ cell lines compared to the p53−/− cell line, along with stabilization of p53 protein. We performed the same experiments in different human colon cancer cell lines and confirmed that MyD88 inhibition induces a p53 dependent apoptosis in theses cell lines, suggesting that this could be a general mechanism, at least in the colon.

Then we generated HCT116 p53+/+ or p53−/− stably expressing a doxycyclin-inducible MyD88 shRNA. These cell lines were subcutaneously implanted in nude mice, then the mice were treated or not with doxycyclin to induce MyD88 extinction in the tumor. This experiment showed that MyD88 inhibition in tumor cells blocks tumor growth in vivo.

Example 2: MyD88 Role in the Maintenance of Genomic Integrity

MyD88 is required for Ras/ERK signaling pathway. It is known that MAPK pathway is implicated in inducing DNA repair mechanisms. Therefore we postulated that upon MyD88 inhibition, the decrease in ERK phosphorylation will induce a lack in the DNA repair mechanisms inducing DNA damage accumulation and triggering a p53 dependent apoptosis. Our data confirm this hypothesis. In fact, transfection of HCT116 p53+/+ shMyD88 cells with a plasmid expressing constitutively activated MEK kinase reduces their apoptosis induced upon doxycyclin treatment, indicating that MyD88 extinction induced apoptosis is due to MAPK pathway inhibition. MAPK pathway is implicated in DNA repair mechanisms, especially in the regulation of some genes implicated in DNA repair like ERCC1 protein; therefore we quantified ERCC1 protein levels upon MyD88 inhibition. We observe a decrease in ERCC1 protein levels and an accumulation of pH2AX, indicating accumulation of double strand DNA damage.

If MyD88 extinction compromises some DNA repair systems, so induction of DNA damage in cancer cells using genotoxic chemotherapy agents should highly increase apoptosis in absence of MyD88 in these cells. And in fact we showed that MyD88 inhibition synergistically amplifies apoptosis induced by DNA damage chemotherapy agent and not chemotherapy acting on other pathways.

Example 3: Screening for Compounds Inhibiting the Interaction Between MyD88 and ERK MAP Kinase Our objective is to select from different libraries small molecules or peptides capable of inhibiting MyD88 interaction with phospho-ERK. Based on our data, we know that overexpression of Myd88 in a cell induces the activation of both ERK and Nf-kB pathways, illustrated by ERK phosphorylation, NF-kB nuclear translocation, and activation of downstream transcription factors. We therefore designed a two-step screening technique.

We are using cell lines (HCT116, A375, Hela) stably expressing at the same time two different constructs:
1—Luciferase cDNA under the control of the SRE promoter (ERK pathway) or the Nf-kB promoter (Nf-kB pathway).
2—MyD88 cDNA under the control of an antibiotic-inducible promoter (Doxycyclin).

In these cells, 24 h upon addition of doxycyclin in the culture media, we will induce the overexpression of MyD88 and activate both ERK and Nf-kB pathways, activating therefore the luciferase activity.

To evaluate the effect of a small molecules or peptides, on MyD88 interactions, candidate molecules will be added at the same time as the doxycyclin in the media, and luciferase activity will be monitored 24 h later. At this stage we observe 4 different outcomes as shown below:

| | Luciferase activity in cells expressing SRE-Luc | Luciferase activity in cells expressing Nf-kB Luc | Biological relevance |
|---|---|---|---|
| Case 1 | Yes | Yes | NO inhibitory activity for the molecule |
| Case 2 | YES | NO | Specific inhibition of MyD88 - IRAK 1 interaction. |
| Case 3 | NO | YES | Specific inhibition of MyD88 - ERK interaction. |
| Case 4 | NO | NO | Inhibition of MyD88 interaction in both pathways. |

This test can be adapted to fit in high throughput screen analysis.

The molecules detected in the first screening test as showing inhibiting capacities for MyD88-ERK interactions, are used in a second functional test based on a focus formation assay. It is known that NIH3T3 immortalized fibroblasts can be transformed by the transfection of the combination of Ras and Myc oncogenes. We show that the replacement of Ras by MyD88 can also induce transformation, but a mutated form of MyD88 unable to bind ERK fails in inducing transformation. The readout for this assay is crystal violet staining.

Based on these data, NIH3T3 cells are transfected with MyD88 and the Myc oncogene, and treated at the same time with the selected molecules from the first screening, and focus formation is monitored. If a molecule is able to block MyD88-ERK interaction, this blocks the focus formation.

Example 4: Combination Tests

The combination tests were performed on the HCT116 p53+/+ or p53−/− shMyD88 cells line, where MyD88 extinction is obtained after 48 h of doxycyclin treatment. Four different chemotherapy agents were used (Cisplatin, Oxaliplatin, Etoposide, and Pacitaxel). Each combination assay is composed of three sets:
Set 1=Cells+Doxycyclin alone
Set 2=Cells+Chemotherapy alone
Set 3=Cells+Doxycyclin+chemotherapy.

Each set contains a range of 5 different concentrations (performed in duplicates) as following:
Doxycyclin treatment: 0-1-2-4-8-16 µg/ml.
Cisplatin treatment: 0-6, 25-12, 5-25-50-100 µM.
Oxaliplatin treatment: 0-8, 75-17, 5-35-70-140 µM.
Etoposide treatment: 0-520, 5-1041-2082-4164-8328 nM.
Pacitaxel treatment: 0-4, 5-9-18-36-72 nM.

At day 0 HCT116 shMyd88 p53+/+ or p53−/− cells lines were plated in 96 well plates at 10000 cell/well.

At day 1, Cells of Set 1 and 3 were treated with doxycyclin, and set 2 cells were left in culture media.

At day 3, Set 1 cells were left in media containing doxycyclin, set 2 and 3 cells were treated with chemotherapy.

At Day 6 the percentage of viable cells in each well was measured by an MTS test. Raw data were analyzed using CompuSyn software and combination indexes were generated indicating the presence or absence of synergy. The results demonstrate that Myd88 silencing synergizes with DNA damage inducing chemotherapy.

Combination index for various combination conditions between MyD88 silencing (Doxycyclin treatment) and different agents of chemotherapy in HCT116 p53+/+ or p53−/− DOX inducible shMyD88 cells are shown in the table below.

| Combination | Combination Index (CI) | | | |
|---|---|---|---|---|
| | HCT116 p53+/+ shMyD88 | | HCT116 p53−/− shMyD88 | |
| | ED50 | ED90 | ED50 | ED90 |
| Doxycyclin-Cisplatin | 0.80617 | 0.55211 | 0.77924 | 0.33163 |
| Doxycyclin-Oxaliplatin | 1.31915 | 0.34733 | 2.57479 | 0.79354 |
| Doxycyclin-Etoposide | 1.29922 | 3.88214 | 6.94130 | 1.53727 |
| Doxycyclin-Pacitaxel | 1.72610 | 6.14818 | 3.18398 | 3.32329 |

Synergy = IC < 1
No synergy = IC > 1

Example 5: In Vivo Combination Assay Protocol

HCT116 p53+/+ shMyD88 cells were subcutaneously injected into the flank of nude mice. After tumor initiation (200 mm3), four groups of mice were created:
Control group: mice receiving Glucose 3% in drinking water.
Doxycyclin group: mice receiving Glucose 3%+Doxycyclin 2 mg/ml in drinking Water.
Cisplatin group: mice receiving Glucose 3% in drinking water and every two day Intra-peritoneal injection of cisplatin at a dose of 0.5 mg/kg.
Combination group: mice receiving Glucose 3%+Doxycyclin 2 mg/ml in drinking water and every two day Intra-peritoneal injection of cisplatin at a dose of 0.5 mg/kg.
Tumor volume was measured every 3 days and monitored till the end of the protocol.

Example 6: Assays for Measuring the Inhibition of the Interaction Between MYD88 and ERK MAP KINASE 1) Proximity Ligation Assay:
Proximity ligation assay is used to determine endogenous protein-protein interaction, based on two primary antibodies raised in different species that recognize the target antigens. Species-specific secondary antibodies, called PLA probes, each with a unique short DNA strand attached to it, bind to the primary antibodies.
When the PLA probes are in close proximity (<40 nm), the DNA strands can interact through a subsequent addition of two other circle-forming DNA oligonucleotides. After joining of the two added oligonucleotides by enzymatic ligation, they are amplified via rolling circle amplification using a polymerase.
Therefore, several-hundred fold replication of the DNA circle has occurred, and labeled complementary oligonucleotide probes highlight the product. The resulting high concentration of fluorescence in each single-molecule amplification product is easily visible as a distinct bright dot when viewed with a fluorescence microscope.
Detailed Protocol:
Cells were stimulated with 10% FCS for 5 and 10 minutes, fixed with 4% PFA, permeabilized and blocked with 0.3% saponin, 10% BSA in PBS.
Then cells were incubated overnight with primary antibodies to MyD88 (Assay Designs) and p-ERK (Sigma-Aldrich).
After 3 PBS 1× wash, cells were incubated with the appropriate, DNA-linked secondary antibodies (PLA) for 2 hours at 37° C.
After 2 PBS 1× wash hybridization solution is added 15 min at 37° C.
After 2 TBS-T wash, Duolink polymerase is added for 90 min at 37° C.
After 2 TBS-T wash, Detection solution is added for 60 min at 37° C.
Then 2 min washes are made sequentially as cited: SSC 2×, SSC 1×, SSC 0.2×, SSC 0.02× and EtOH 70%.
Cells are mounted using Duolink Mounting medium.
2) Immunoprecipitation Assay:
Immunoprecipitation assay is used to visualize protein-protein interaction.
Seed $3.10^6$ HEK293T cells in 10 cm plates.
After 24 h, transfect the HEK293T by 3 μg of the plasmid of interest.
48 h after Transfection cells are Harvested, and lysed using a lysis buffer containing: 1% NP40, 20 mM Tris pH 7.5, 150 mM NaCl, and 2 mM EDTA.
After lysis and protein dosage, 1-2 mg of proteins per condition is used to perform the immunoprecipitation experiment.
The lysates are incubated with 30 μL of protein A sepharose beads for 30 minutes on the rotator at 4° C.
Centrifuge the tubes for 5 minutes at 2000 rpm at 4° C.
Transfer the supernatants into new tubes.
Add 2-5 ug of the antibody to the pre-cleared lysates. Incubate for 2-4 hours on the rotator at 4° C.
Add 50 μL of protein A sepharose beads. Incubate the tubes on the rotator for 1 hour at 4° C.
Centrifuge for 5 minutes at 2000 rpm at 4° C. Throw the supernatant, and keep the beads.
Wash the beads 3-4 times with 1 mL lysis buffer. Centrifuge for 5 minutes at 2000 rpm at 4° C.
Add 50 μL of Laemelli 2× buffer to the beads in order to elute the proteins.
The interaction between the 2 proteins is visualized by WB.

REFERENCES

Rakoff-Nahoum S. et al. 2007. *Science*
Coste I et al. 2010 *J Clin Invest*
Dai Y et al. 2008. *Blood*
Yacoub A. et al. 2003. *Radiat Res*

The invention claimed is:

1. An in vitro method for selecting compounds capable of potentiating the effect of a DNA damage inducing chemotherapy agent for the treatment of cancer comprising the following steps:
   a) providing at least one candidate compound;
   b) providing transformed cells expressing stably MyD88 under the control of an inducible promoter and expressing a reporter gene under the control of a promoter from the MAPK pathway selected from the group consisting of an SRE promoter, an ELK promoter and a MyC promoter;
   c) inducing overexpression of MYD88 in the transformed cells in the presence of the at least one candidate compound;
   d) measuring the expression of the reporter gene and selecting the at least a one candidate compound when the at least one candidate compound inhibits the expression of the reporter gene;
   e) providing immortalized fibroblasts transformed by transfection with the MyD88 and Myc oncogenes; and
   f) in a focus formation assay, monitoring focus formation in the presence of the at least one candidate compound that inhibits expression of the reporter gene selected in step d) and in the presence of at least one DNA damage inducing chemotherapy agent, and selecting the at least one compound when the at least one compound potentiates the inhibitory effect of the DNA damage inducing chemotherapy agent on the focus formation;
   wherein the DNA damage inducing chemotherapy agent is selected from the group consisting of oxaliplatin, cisplatin, carboplatin, doxorubicin, etoposide, bleomycin and mixtures thereof.

2. The method according to claim 1, wherein in step b) the promoter from the MAPK pathway is the SRE promoter.

3. The method according to claim 1, wherein the method further comprises the following steps:
- providing transformed cells expressing stably MyD88 under the control of an inducible promoter and expressing a reporter gene under the control of a promoter from inflammation pathway selected from the group consisting of an Nf-kB promoter and an ISRE promoter;
- inducing overexpression of MYD88 in the transformed cells in the presence of the at least one candidate compound; and
- measuring the expression of the reporter gene and selecting the compound which does not inhibit the expression of the reporter gene.

4. The method according to claim 3, wherein the promoter from the inflammation pathway is Nf-kB.

5. The method according to claim 1, wherein in step b) the cells are selected from the group consisting of a HCT116 cell line, an A375 cell line and a HeLa cell line.

6. The method according to claim 1, wherein the inducible promoter is an antibiotic-inducible promoter.

7. The method according to claim 1, wherein the immortalized fibroblasts are NIH3T3 immortalized fibroblasts.

8. The method according to claim 1, wherein the cancer is selected from the group consisting of colorectal cancer, intestinal cancer, melanoma, lung cancer and cervical cancer.

9. The method according to claim 1, wherein the at least one candidate compound provided at step a) is selected at step d) according to a method comprising:
- contacting the at least one candidate compound with a ERK MAPK protein and a MyD88 protein, under conditions suitable to allow ERK MAPK and the MyD88 to interact in the absence of the at least one candidate molecule;
- determining when the ERK MAPK interacts with the MyD88 as measured in the presence and in the absence of the at least one candidate compound; and
- selecting at least one candidate compound that inhibits the interaction of ERK MAPK and MyD88.

10. An in vitro method for selecting compounds capable of potentiating the effect of a DNA damage inducing chemotherapy agent for the treatment of cancer comprising the following steps:
- providing transformed cells expressing stably MyD88 under the control of an inducible promoter and expressing a reporter gene under the control of a promoter from the MAPK pathway selected from the group consisting of an SRE promoter, an ELK promoter and a MyC promoter, wherein, in the absence of a compound that blocks the interaction of MyD88 with ERK MPAK, activating the inducible promoter results in the expression of MyD88, which activates the promoter from the MAPK pathway to induce expression of the reporter gene;
- inducing overexpression of MYD88 in the transformed cells in the presence of a candidate compound;
- measuring the expression of the reporter gene; and
- initially selecting the candidate compound when said candidate compound inhibits the expression of the reporter gene;
- growing immortalized fibroblasts transformed by transfection with MyD88 and Myc oncogenes;
- contacting the immortalized fibroblasts with the candidate compound and a DNA damage inducing chemotherapy agent in a focus formation assay;
- monitoring the immortalized fibroblasts in said assay for focus formation; and
- finally selecting the candidate compound when the candidate compound potentiates the effect of the DNA damage inducing chemotherapy agent such that no foci are formed, wherein the DNA damage inducing chemotherapy agent is selected from the group consisting of oxaliplatin, cisplatin, carboplatin, doxorubicin, etoposide, bleomycin and mixtures thereof.

* * * * *